United States Patent [19]

Symon et al.

[11] 3,936,473

[45] Feb. 3, 1976

[54] VINYLATION OF AROMATIC COMPOUNDS

[75] Inventors: Ted Symon, Lombard; Nils J. Christensen, Palatine, both of Ill.

[73] Assignee: Universal Oil Products Company, Des Plaines, Ill.

[22] Filed: Aug. 9, 1973

[21] Appl. No.: 387,087

[52] U.S. Cl............ 260/343.2 R; 252/522; 260/410; 260/486 R; 260/488 R
[51] Int. Cl.².............. C07D 311/08; C07D 311/10
[58] Field of Search .............................. 260/343.2 R

[56] References Cited
UNITED STATES PATENTS

| | | | |
|---|---|---|---|
| 3,008,969 | 11/1961 | Pretka.......................... | 260/343.2 R |
| 3,259,635 | 7/1966 | Ritter et al................... | 260/343.2 R |
| 3,803,175 | 4/1974 | Sparks et al. ................ | 260/343.2 R |

*Primary Examiner*—John D. Randolph
*Attorney, Agent, or Firm*—James R. Hoatson, Jr.; Raymond H. Nelson; William H. Page II

[57] ABSTRACT

The activity of a catalyst system comprising a salt of a noble metal of Group VIII of the Periodic Table, a salt of copper, an organic acid and an oxygen-containing gas which is utilized in the vinylation of aromatic compounds may be enhanced by effecting the reaction in the presence of a compound containing an active methylene group.

12 Claims, No Drawings

VINYLATION OF AROMATIC COMPOUNDS

This invention relates to a process for the vinylation of an aromatic compound in the presence of certain catalytic compositions of matter and a compound containing an active methylene group. More specifically the invention is concerned with effecting the vinylation of an aromatic compound in the presence of a catalyst system and a compound containing an active methylene group whereby the activity of the vinylation catalyst is greatly enhanced.

It is known in the prior art that aromatic compounds may be subjected to a vinylation reaction by treatment with an ethylenic compound in the presence of certain catalyst systems to obtain a vinylated aromatic compound. For example, phenol may be treated with an ethylenic compound such as methyl acrylate in the presence of a catalyst system comprising a mixture of a salt of a noble metal of Group VIII of the Periodic Table, a salt of a transition series metal, an oxygen-containing gas in a solvent medium which comprises an organic acid to prepare vinylated aromatic compounds such as coumarin. The vinylated aromatic compounds which are thus prepared comprise aromatic compounds containing a substituent which possesses an ethylenic linkage and thus will be useful in the chemical industry, and particularly the aroma industry. For example, methyl cinnamate which possesses a balsamic odor, may be prepared according to the vinylation process. Another compound which may be prepared by the vinylation process comprises β-stearyl acetate which may be subsequently hydrogenated to form β-phenylethyl acetate, this compound being thereafter hydrolyzed to form β-phenylethanol which possesses an aroma of attar of rose. Another compound prepared by the hydrolysis of β-stearyl acetate is phenylacetaldehyde, this compound adding flower aromas such as hyacinth, jonquil or narcissus notes to fragrance chemicals. In addition, another compound which may be prepared by the vinylation process is 2-(2-hydroxyphenyl)acrylic acid which may be converted to coumarin, said coumarin possessing a fragrant odor similar in nature to vanilla and which is used as a deodorizing and odor enhancing agent in perfumes, soaps, tobaccos, inks, rubber and other products where aromatic properties are required. Furthermore, coumarin itself may be prepared by, as hereinbefore set forth, treating phenol with methyl acrylate to form coumarin and/or o-methyl coumarate, the latter compound then being cyclized to form coumarin. The aforementioned vinylated aromatic compounds are useful in the preparation of fragrance or aroma compositions which are added to cosmetic and toiletry articles such as perfumes, colognes, soaps, talcs, bath powders, deodorants, aftershave lotions, etc., whereby the aforementioned compounds will possess desirable and pleasing scents.

As hereinafter set forth in greater detail, it will be shown that by effecting the vinylation reaction in the presence of certain compounds, the activity of the catalysts which are used in the reaction will be greatly enhanced, thereby permitting the obtention of greater yields of the desired vinylated aromatic compounds.

It is therefore an object of this invention to provide a process for preparing vinylated aromatic compounds.

A further object of this invention is to provide a process for obtaining improved yields of vinylated aromatic compounds by effecting the reaction of an aromatic compound with a compound containing an ethylenic linkage in a catalytic manner, the activity of the catalyst which is used in the process being increased by effecting the reaction in the presence of certain compounds containing an active methylene group.

In one aspect an embodiment of this invention resides in a process for the vinylation of an aromatic compound which comprises treating an aromatic compound with an olefinic compound at vinylation conditions in the presence of a catalyst system which comprises a salt of a noble metal of Group VIII, a salt of copper, an oxygen-containing gas and an organic acid and recovering the resultant vinylated aromatic compound, the improvement which comprises effecting said vinylation reaction in the presence of a compound containing an active methylene group.

A specific embodiment of this invention is found in a process for the vinylation of an aromatic compound which comprises treating phenol with methyl acrylate at a temperature in the range of from about ambient to about 250° C. and a pressure in the range of from about atmospheric to about 500 atmospheres in the presence of a catalyst comprising palladium acetate, cupric acetate, propionic acid and air and also in the presence of 2,4-pentanedione.

Other objects and embodiments will be found in the following further detailed description of the present invention.

As hereinbefore set forth the present invention is concerned with an improvement in a process for the vinylation of an aromatic compound in which said aromatic compound is treated with a compound containing an ethylenic linkage at vinylation conditions in the presence of a catalyst system of a type hereinafter set forth in greater detail, the improvement which comprises also effecting the reaction in the presence of a compound containing an active methylene group.

Examples of organic compounds which may be reacted in the process will possess the generic formula:

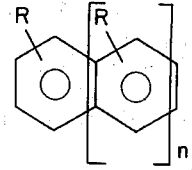

in which R is selected from the group consisting of hydrogen, hydroxyl, alkyl, alkoxyl, aryl, alkaryl, aralkyl, cycloalkyl and halogen (preferably chlorine) radicals and n is an integer of from 0 to about 2. Specific examples of these compounds will include benzene, toluene, ethylbenzene, n-propylbenzene, isopropylbenzene (cumene), n-butylbenzene, sec-butylbenzene, t-butylbenzene, n-amylbenzene, sec-amylbenzene, etc., phenol, o-cresol, m-cresol, p-cresol, 2,3-dimethylphenol, 2,4-dimethylphenol 2,5-dimethylphenol, 2,6-dimethylphenol, 3,4-dimethylphenol, 3,5-dimethylphenol, 2-sec-butylphenol, 3-sec-butylphenol, 4-sec-butylphenol, 2-tert-butylphenol, 4-tert-butylphenol, 2-tert-butyl-4-methylphenol, 2-tert-butyl-5-methylphenol, 4-tert-butyl-2-methylphenol, etc., o-chlorophenol, m-chlorophenol, p-chlorophenol, 2-chloro-4-methylphenol, etc., 2-methoxyphenol, 4-methoxyphenol, etc., anisole, phenetole, propylphenylether, isopropylphenylether, butylphenylether, etc., phenyl-benzene, benzylbenzene, o-tolylbenzene, m-tolylbenzene, p-tolylbenzene, cyclohexylbenzene, cyclopentylbenzene, chlorobenzene, 1-methylnaphthalene, 2-methylnaphthalene, 1,6-dimethylnaphthalene, 1,2-diethylnaphthalene, 1-methoxynaphthalene, 2-methoxynaphthalene, 1,6-methoxynaphthalene, 1,8-methoxynaphthalene, 1-ethoxynaphthalene, 2-ethoxynaphthalene, 1-phenylnaphthalene, 2-phenylnaphthalene, 1-benzylnaphthalene, 1-p-tolylnaphthalene, 2-p-tolylnaphthalene, 1-o-tolylnaphthalene, 1-m-tolylnaphthalene, 1-benzylnaphthalene, 2-benzylnaphthalene, 1-cyclopentylnaphthalene, 2-cyclohexylnaphthalene, 1-chloronaphthalene, 2-chloronaphthalene, 1,6-dichloronaphthalene, the corresponding anthracenes, etc.

The aforementioned aromatic compounds are reacted with an ethylenic compound which possesses the generic formula:

in which X and Y are selected from the group consisting of hydrogen, alkyl,

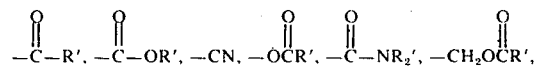

and OR' radicals, R' being selected from the group consisting of hydrogen, alkyl, aryl, cycloalkyl, aralkyl, alkaryl radicals and n is an integer of from 0 to about 16. Some specific examples of these compounds which contain an ethylenic linkage will include methyl vinyl ketone, ethyl vinyl ketone, propyl vinyl ketone, butyl vinyl ketone, methyl propenyl ketone, ethyl propenyl ketone, propyl propenyl ketone, phenyl vinyl ketone, phenyl propenyl ketone, cyclopentyl vinyl ketone, cyclohexyl vinyl ketone, cyclopentyl propenyl ketone, cyclohexyl propenyl ketone, benzyl vinyl ketone, benzyl propenyl ketone, o-tolyl vinyl ketone, m-tolyl vinyl ketone, p-tolyl vinyl ketone, o-tolyl propenyl ketone, m-tolyl propenyl ketone, p-tolyl propenyl ketone, acrolein, acrylic acid, allyl acetate, isobutenyl acetate, isobutenyl propionate, methallyl acetate, methyl acrylate, ethyl acrylate, propyl acrylate, isopropyl acrylate, phenyl acrylate, benzyl acrylate, cyclopentyl acrylate, cyclohexyl acrylate o-tolyl acrylate, m-tolyl acrylate, p-tolyl acrylate, methyl methacrylate, ethyl methacrylate, propyl methacrylate, isopropyl methacrylate, phenyl methacrylate, benzyl methacrylate, cyclopentyl methacrylate, cyclohexyl methacrylate, o-tolyl methacrylate, m-tolyl methacrylate, p-tolyl methacrylate, acrylonitrile, vinyl acetate, vinyl propionate, vinyl benzoate, vinyl cyclohexane, acrylamide, N-methacrylamide, N-ethylacrylamide, N-propylacrylamide, N-isopropylacrylamide, N-phenylacrylamide, N-benzylacrylamide, N-o-tolylacrylamide, N-p-tolylacrylamide, N-cyclopentylacrylamide, N-cyclohexylacrylamide, N,N-dimethylacrylamide, N,N-diethylacrylamide, N,N-dipropylacrylamide, N,N-diisopropylacrylamide, N,N-diphenylacrylamide, N,N-dibenzylacrylamide, N,N-di-o-tolylacrylamide, N,N-di-m-tolylacrylamide, N,N-di-p-tolylacrylamide, N,N-dicyclohexylacrylamide, N,N-dicylopentylacrylamide, etc. It is to be understood that the aforementioned aromatic compounds and compounds containing an ethylenic linkage are only representative of the class of compounds which may be utilized as starting materials, and that the present invention is not necessarily limited thereto.

The reaction between the aromatic compound and the ethylenic compound of the type hereinbefore set forth in greater detail is effected in the presence of a catalyst. In the preferred embodiment of the invention the catalyst will comprise a system consisting of a salt of a noble metal of Group VIII of the Periodic Table, a salt of a transition series metal, and preferably copper, an oxygen-containing gas such as oxygen or air and a solvent comprising an organic acid. It is also contemplated within the scope of this invention that other catalysts may also be employed in place of the catalyst system, although not necessarily with equivalent results. Examples of these other catalysts which may be employed will include an organic salt of a metal of Group VIII of the Periodic Table or a catalyst system consisting essentially of a metal of Group VIII of the Periodic Table, a transition series metal and an oxygen-containing gas. In the preferred catalyst system of the present invention, the salts of a noble metal of Group VIII of the Periodic Table will preferably comprise carboxylates or acetylacetonates of these metals. Specific examples of these Group VIII metal salts will include the carboxylates such as palladium acetate, palladium propionate, palladium butyrate, palladium valerate, palladium caproate, platinum acetate, platinum propionate, platinum butyrate, platinum valerate, platinum caproate, rhodium acetate, rhodium propionate, rhodium butyrate, rhodium valerate, rhodium caproate, ruthenium acetate, ruthenium propionate, ruthenium butyrate, ruthenium valerate, ruthenium caproate, osmium acetate, osmium propionate, osmium butyrate, osmium valerate, osmium caproate, iridium acetate, iridium propionate, iridium butyrate, iridium valerate, iridium caproate, nickel acetate, nickel propionate, nickel butyrate, palladium acetylacetonate, platinum acetylacetonate, rhodium acetylacetonate, ruthenium acetylacetonate, osmium acetylacetonate, iridium acetylacetonate, etc. Some specific examples of the salts of copper which may be employed as the second component of the catalyst system will also include the carboxylates and acetylacetonates such as copper acetate, copper propionate, copper butyrate, copper valerate, copper acetylacetonate, etc. As was hereinbefore set forth, the third component of the catalyst system will contain an oxygen-containing gas such as oxygen or air, the latter being preferred due to the readily greater availability and negligible cost therefor.

The vinylation reaction is effected in the presence of a solvent which comprises an organic acid, examples of said acids being acetic acid, propionic acid, butyric acid, valeric acid, isobutyric acid, isovaleric acid, caproic acid, oenanthylic acid, caprylic acid, pelargonic acid, capric acid, etc. Again, in the preferred embodiment of the invention, the acid solvent which is used will be acetic acid or propionic acid due to the greater availability and lower cost thereof.

The reaction conditions under which the process of this invention is effected will include temperatures ranging from ambient (about 20° to 25° C.) up to about 250° C. or more. In addition the reaction pressure at which the aromatic compound is reacted with the ethylenic compound will range from about atmospheric up to about 500 atmospheres or more, the superatmospheric pressures usually being supplied by the introduction of the oxygen-containing gas into the reaction vessel. However, it is also contemplated within the scope of this invention that the oxygen-containing gas may afford only a partial pressure of the total desired reaction pressure, the remainder of said pressure being provided for by the introduction of a substantially inert gas such as nitrogen into the reaction zone.

As will be hereinafter set forth in greater detail in the examples at the end of the specification, we have now discovered that by effecting the reaction in the presence of a compound containing an active methylene group, the activity and efficiency of the catalyst system will be greatly enhanced thereby permitting a more rapid recovery of the desired product. The activity of the catalyst is maintained until all of the olefinic compound is consumed, which is in contrast to the behavior of a catalyst system in a reaction in which no compound containing an active methylene group is present, the activity of the catalyst system decreasing over an extended period of time without the total consumption of the olefinic compound.

Examples of compounds which possess active methylene groups which may be utilized to increase the catalytic activity of the catalyst system according to the process of the present invention will include such compounds as methyl acetoacetate, ethyl acetoacetate, n-propyl acetoacetate, isopropyl acetoacetate, n-butyl acetoacetate, amyl acetoacetate, hexyl acetoacetate, heptyl acetoacetate, etc., methyl propioacetate, ethyl propioacette, n-propyl propioacetate, isopropyl propioacetate, n-butyl propioacetate, amyl propioacetate, hexyl propioacetate, heptyl propioacetate, etc., methyl butyroacetate, ethyl butyroacetate, n-propyl butyroacetate, isopropyl butyroacetate, n-butyl butyroacetate, amyl butyroacetate, hexyl butyroacetate, heptyl butyroacetate, etc., dimethyl malonate, diethyl malonate, dipropyl malonate, dibutyl malonate, dipentyl malonate, etc.; β-diketones possessing the generic formula:

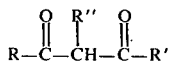

in which R and R' comprise alkyl containing compounds from 1 to about 4 carbon atoms and R'' is selected from the group consisting of hydrogen, alkyl, cycloalkyl, aryl, alkaryl and aralkyl radicals such as 2,4-pentanedione, 2,4-hexanedione, 2,4-heptanedione, 2,4-octanedione, 3,5-heptanedione, 3,5-octanedione, 3,5-nonanedione, 4,6-nonanedione, 3-methyl-2,4-pentanedione, 3-ethyl-2,4-pentanedione, 3-cyclopentyl-2,4-pentanedione, 3-benzyl-2,4-pentanedione, 3-p-tolyl-2,4-pentanedione, 3-methyl-2,4-hexanedione, 3-cyclopentyl-2,4-hexanedione, 3-phenyl-2,4-hexanedione, 4-ethyl-3,5-heptanedione, 4-p-tolyl-3,5-heptanedione, 4-cyclohexyl-3,5-nonanedione, 4-propyl-3,5-nonanedione, 1-phenyl-1,3-butanedione, 1,3-cyclopentanedione, 1,3-cyclohexanedione, 1,3-cycloheptanedione, 1,3-cyclooctanedione, 2-acetylcyclopentanone, 2-acetylcyclohexanone, etc.; benzyl ketones such as methyl benzyl ketone, ethyl benzyl ketone, propyl benzyl ketone, butyl benzyl ketone, etc. As in the case of the aromatic compounds and the ethylenic compounds, it is also understood that the aforementioned compounds containing an active methylene group are only representative of the class of compounds which may be used, and that the present invention is not necessarily limited thereto. The aforementioned compounds containing an active methylene group may be present in a range of from about 0.1:1 to about 10:1 moles of compound containing an active methylene group per mole of noble metal of Group VIII of the Periodic Table.

The process of this invention may be effected in any suitable manner and may be effected in either a batch or continuous type operation. For example when a batch type operation is used, a quantity of the aromatic compound and the compound containing an ethylenic or olefinic linkage is placed in an appropriate apparatus along with the particular catalyst system which is used. In addition, the compound containing an active methylene group is also added to the apparatus along with the organic acid solvent. This apparatus may, in the preferred embodiment of the invention, comprise an autoclave of the rotating or mixing type. The autoclave is then sealed and the oxygen-containing gas is charged thereto until the desired operating pressure has been reached. Thereafter the apparatus is then heated to the desired operating temperature and maintained at the predetermined conditions of temperature and pressure for a residence time which may range from about 0.5 up to about 40 hours or more in duration. At the end of this period, heating is discontinued and the apparatus and contents thereof are allowed to return to room temperature. Thereafter any excess pressure, if any, is discharged and the autoclave is opened. The reaction mixture is recovered therefrom and then subjected to conventional means of separation and purification, said means including filtration to separate any solid catalyst followed by washing with water, drying over sodium sulfate, evaporation, fractional crystallization, fractional distillation, etc. whereby the desired product comprising a vinylated aromatic compound is recovered. By utilizing the added feature of effecting the reaction in the presence of a compound containing an active methylene group, it will be possible to considerably shorten the residence time during which the vinylation reaction takes place, said shortened residence time being accompanied by a complete consumption of the olefinic charge stock.

It is also contemplated within the scope of this invention that the vinylation process may be effected in a continuous manner of operation. When such a type of operation is used, a quantity of the aromatic compound and the ethylenic compound are continuously charged to a reactor which contains the particular catalyst system and the compound containing an active methylene group, said reactor being maintained at the desired operating conditions of temperature and pressure. In addition, the oxygen-containing gas and the organic acid solvent are continuously charged to the reactor through separate lines or, if so desired, one or both of the reactants may be admixed with the solvent prior to entry into said reactor and the resulting mixture charged thereto in a single stream. Upon completion of the desired residence time, the reactor effluent is continuously withdrawn from the reactor and subjected to separation and purification processes similar in nature to those set forth above. In these separation and purification processes the desired vinylated aromatic compound is separated from any unreacted aromatic compound, unreacted ethylenic compound, solvent and undesired isomers. The unreacted starting material and solvent may be recycled to form a portion of the feed stock. When utilizing a solid catalyst system, it is possible to effect the continuous manner of operation in various ways. For example, one such method is to utilize the catalyst as a fixed bed in the reactor and pass the reactants through said catalyst bed in either an upward or downward flow. Another method of effecting the reaction is to utilize the solid catalyst system in a moving bed type operation whereby the reactants in the solvent medium in the presence of the compound containing an active methylene group are passed through the reaction zone either concurrently or countercurrently to each other, while yet another method is the slurry type operation in which the catalyst is carried into the reaction zone as a slurry in one or both of the reactants.

Examples of compounds which have been prepared according to the process of this invention will include coumarin, 2-phenylvinyl acetate, 2-phenylvinyl propionate, 2-phenylvinyl butyrate, 2-phenylvinyl valerate, 2-(2-hydroxyphenyl)vinyl acetate, 2-(2-methoxyphenyl)vinyl acetate, 2-methyl-3-phenylacrylic acid methyl ester, 2-methyl-3-(2-hydroxyphenyl)-acrylic acid methyl ester, 2-methyl-3-(2-methoxyphenyl)acrylic acid methyl ester, 3-(phenyl)acrylic acid, 3-(2-hydroxyphenyl)acrylic acid, 3-(2-methoxyphenyl)acrylic acid, 3-(2-chlorophenyl)acrylic acid, 3-(2-bromophenyl)acrylic acid, etc.

The following examples are given to illustrate the process of the present invention which, however, are not intended to limit the generally broad scope of the present invention in strict accordance therewith.

EXAMPLE I

In this example 282 grams (3.0 mole) of phenol, 104 grams (1.2 mole) of methyl acrylate along with 2.8 grams (0.012 mole) of palladium acetate, 4.8 grams (0.024 mole) of cupric acetate monohydrate and 6 grams of Celite were placed in a solvent mixture comprising 65 grams of propionic acid and 65 grams of cyclohexane. The reaction mixture was charged to a 1-liter stainless steel, stirred autoclave which was then sealed. The autoclave was then pressured with 250 pounds per square inch with air, the autoclave was heated to a temperature of 90° C. and maintained thereat as air was passed through the system at a rate of about 1 standard cubic foot per hour. At the end of the vinylation period, the air was replaced with nitrogen and the temperature was increased to 130° C. for a period of 1 hour to cause a precipitation of the palladium metal. The catalyst which was very active during the first hour of the reaction, rapidly deactivated and it took a period of 9 hours to reach a 90% conversion of the methyl acrylate. Qualitative gas-liquid chromatography indicated that at a 70% methyl acrylate conversion there was a 41% selectivity to o-methyl coumarate and coumarin in which the ratio of o-methyl coumarate to coumarin was 0.7:1, while the ratio of o-methyl coumarate to p-methyl coumarate was 2.3:1.

EXAMPLE II

In this example the above experiment was repeated using identical proportions of reactants, solvent and catalyst, the only difference being that 48 millimoles of 2,4-pentanedione was added to the reaction mixture. The autoclave was again sealed, pressured with 250 pounds per square inch of air and heated to a temperature of 90° C. as air was passed through the system at a rate of about 1 standard cubic foot per hour. The addition of the 2,4-pentanedione disclosed that, in contradistinction to the above experiment, the reaction rate increased after a period of 2 hours and the reaction continued at the increased rate until all of the methyl acrylate had reacted after a period of 5 hours. Preparative gas-liquid chromatography disclosed that at 70% methyl acrylate conversion, there was a 47% selectivity to o-methyl coumarate and coumarin, the ratio of o-methyl coumarate to coumarin was 0.8:1 while the ratio of o-methyl coumarate to p-methyl coumarate was 3.2:1. It is to be noted that in addition to the shorter reaction time in which the methyl acrylate was converted, there was also a higher ratio of o-methyl coumarate to p-methyl coumarate. This is a desirable feature of the reaction inasmuch as the o-methyl coumarate can be cyclized and converted to coumarin while the p-methyl coumarate cannot and thus constitutes an unwanted side product in the reaction.

EXAMPLE III

In this example 324 grams (3.0 mole) of o-cresol, 104 grams (1.2 mole) of methyl acrylate, 0.012 mole of palladium acetylacetonate, 0.024 mole of cupric acetate and 6 grams of Celite are placed in a solvent mixture comprising 65 grams of acetic acid and 65 grams of cyclohexane. The reaction mixture is then charged to a 1-liter stainless steel autoclave which is sealed and air is pressed in until an initial operating pressure of 250 pounds per square inch is reached. The autoclave is then heated to a temperature of 110° C. and maintained thereat as air was passed through the system at a rate of about 1 standard cubic foot per hour for a period of time until all of the methyl acrylate is consumed.

The above experiment is repeated utilizing the same amounts of reactants, catalyst and solvent, there being added to said reaction mixture 50 millimoles of methyl acetoacetate. When the autoclave is pressured by charging air thereto and heated to a temperature of 100° C., it will be found that the reaction time during which the methyl acrylate is consumed will be considerably shorter than the reaction time needed to effect the reaction of paragraph one whereby the desired product comprising 8-methylcoumarin is obtained.

EXAMPLE IV

To a stainless steel autoclave is added a mixture of 234 grams (3.0 mole) of benzene, 120 grams (1.2 mole) of allyl acetate, 0.012 mole of palladium acetylacetonate, 0.024 moles of cupric acetate monohydrate, 6 grams of Celite along with a solvent system comprising 130 grams of acetic acid. In addition 50 millimoles of dimethyl malonate is also placed in the reactor which is thereafter sealed and pressed with air until a pressure of 300 pounds per square inch is reached. The autoclave is then heated to a temperature of 100° C. and maintained thereat as air was passed through the system at a rate of about 1 standard cubic foot per hour until the allyl acetate is consumed. Following this the autoclave is purged with nitrogen and heated to a temperature of 130° C. for an additional hour in order to precipitate the palladium. Recovery of the product and analysis by means of gas-liquid chromatography will disclose the presence of the desired product comprising cinnamyl acetate with a complete consumption of the allyl acetate.

When the above experiment is repeated omitting the dimethyl malonate, it will be found that a considerably longer reaction time is required in order to consume the allyl acetate and obtained the desired cinnamyl acetate in desirable yields.

EXAMPLE V

In this experiment 234 grams (3.0 moles) of benzene, 103 grams (1.2 moles) of vinyl acetate along with 0.012 mole of platinum acetylacetonate, 0.024 mole of cupric propionate, 6 grams of Celite and a solvent comprising 130 grams of propionic acid is placed in an autoclave along with 50 millimoles of 2,4-hexanedione. The autoclave is sealed and pressed with 250 pounds per square inch with air, after which the autoclave is heated to a temperature of 100° C. and maintained thereat as air was passed through the system at a rate of about 1 standard cubic foot per hour. After a predetermined residence time has elapsed, the air is purged from the autoclave by passage of nitrogen therethrough following which the autoclave is heated to a temperature of 130° C. in order to precipitate the platinum. The autoclave is then cooled, the excess pressure is discharged and the reaction mixture is recovered therefrom. Analysis by means of gas-liquid chromatography will establish the fact that the vinyl acetate has been consumed with a desirable yield of 2-phenylvinyl acetate being obtained therefrom.

In contradistinction to the results obtained in the above paragraph, when the experiment is repeated utilizing similar quantities of reactants, catalyst and solvent but omitting the presence of the 2,4-hexanedione, it will be found that a considerably longer reaction time is required in order to obtain similar results.

We claim as our invention:

1. In a process for the preparation of a coumarin which comprises reacting a hydroxy substituted aromatic compound possessing the generic formula:

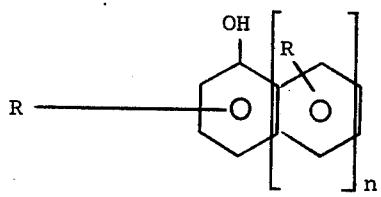

in which R is selected from the group consisting of hydrogen, hydroxyl, alkyl, alkoxyl, aryl, alkaryl, aralkyl, cycloalkyl and halogen radicals and n is an integer of from 0 to about 2 with an ethylenic compound which possesses the generic formula:

in which X and Y are selected from the group consisting of hydrogen, alkyl,

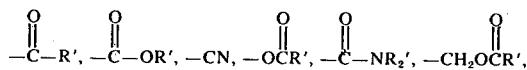

and OR' radicals, R' being selected from the group consisting of hydrogen, alkyl, aryl, cycloalkyl, aralkyl, alkaryl radicals and n is an integer of from 0 to about 16 at a temperature in the range of from about ambient to about 250° C. and a pressure in the range of from atmospheric to about 500 atmospheres in the presence of a catalyst system comprising an acetylacetonate or carboxylate salt of copper or a noble metal of Group VIII of the Periodic Table, oxygen, and organic acid and recovering the resultant coumarin compound, the improvement which comprises effecting said vinylation reaction in the presence of a compound containing an active methylene group selected from the group consisting of lower alkyl acetoacetate; lower alkyl propioacetate; lower alkyl butyroacetate; diloweralkyl malonate: β-diketones possessing the generic formula:

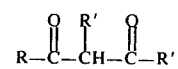

in which R and R' comprise alkyl containing compounds from 1 to about 4 carbon atoms and R'' is selected from the group consisting of hydrogen, alkyl, cycloalkyl, aryl, alkaryl and aralkyl radicals and benzyl ketones present in a range of from about 0.1:1 to about 10:1 moles of said active methylene group-containing compound per mole of noble metal of Group VIII of the Periodic Table or copper.

2. The process as set forth in claim 1 in which said compound containing an active methylene group is methyl acetoacetate.

3. The process as set forth in claim 1 in which said compound containing an active methylene group is dimethyl malonate.

4. The process as set forth in claim 1 in which said compound containing an active methylene group is a β-diketone.

5. The process as set forth in claim 4 in which said β-diketone is 2,4-pentanedione.

6. The process as set forth in claim 4 in which said β-diketone is 2,4-hexanedione.

7. The process as set forth in claim 4 in which said β-diketone is 3-methyl-2,4-pentanedione.

8. The process as set forth in claim 1 in which said aromatic compound is phenol, said olefinic compound is methyl acrylate and said vinylated aromatic compound is coumarin.

9. The process as set forth in claim 1 in which said aromatic compound is o-cresol, said olefinic compound is methyl acrylate and said vinylated aromatic compound is 8-methylcoumarin.

10. The process as set forth in claim 1 in which said catalyst system comprises palladium acetate, cupric acetate, acetic acid and air.

11. The process as set forth in claim 1 in which said catalyst system comprises palladium acetylacetonate, cupric acetate, acetic acid and air.

12. The process as set forth in claim 1 in which said catalyst system comprises platinum acetylacetonate, cupric propionate, propionic acid and air.

* * * * *